(12) United States Patent
Zheng et al.

(10) Patent No.: US 12,107,228 B2
(45) Date of Patent: Oct. 1, 2024

(54) NON-AQUEOUS ELECTROLYTE FOR A LITHIUM ION BATTERY AND LITHIUM ION BATTERY

(71) Applicant: SHENZHEN CAPCHEM TECHNOLOGY CO., LTD., Guangdong (CN)

(72) Inventors: Zhongtian Zheng, Guangdong (CN); Ling Zhong, Guangdong (CN); Shiguang Hu, Guangdong (CN); Kai Tu, Guangdong (CN); Qiao Shi, Guangdong (CN); Dejun Xiong, Guangdong (CN)

(73) Assignee: SHENZHEN CAPCHEM TECHNOLOGY CO., LTD., Shenzhen (CN)

( * ) Notice: Subject to any disclaimer, the term of this patent is extended or adjusted under 35 U.S.C. 154(b) by 721 days.

(21) Appl. No.: 17/417,111

(22) PCT Filed: Jan. 2, 2020

(86) PCT No.: PCT/CN2020/070004
§ 371 (c)(1),
(2) Date: Jun. 21, 2021

(87) PCT Pub. No.: WO2020/140923
PCT Pub. Date: Jul. 9, 2020

(65) Prior Publication Data
US 2022/0109191 A1   Apr. 7, 2022

(30) Foreign Application Priority Data
Jan. 2, 2019 (CN) .......................... 201910002263.9

(51) Int. Cl.
*H01M 10/0569* (2010.01)
*H01M 4/505* (2010.01)
*H01M 4/525* (2010.01)
*H01M 10/0525* (2010.01)

(52) U.S. Cl.
CPC ....... *H01M 10/0569* (2013.01); *H01M 4/505* (2013.01); *H01M 4/525* (2013.01); *H01M 10/0525* (2013.01); *H01M 2300/0034* (2013.01)

(58) Field of Classification Search
CPC .. H01M 10/0569; H01M 4/505; H01M 4/525; H01M 10/0525; H01M 2300/0034; H01M 4/5805; H01M 2300/0025; H01M 10/0568; H01M 10/052; H01M 10/0567; H01M 10/4235; Y02E 60/10; C07D 327/04; C07D 497/04
See application file for complete search history.

(56) References Cited

U.S. PATENT DOCUMENTS

2016/0359196 A1* 12/2016 Kim .................. H01M 10/0569

FOREIGN PATENT DOCUMENTS

| CN | 104466246 A | 3/2015 | |
|----|----|----|----|
| CN | 106252710 A | 12/2016 | |
| CN | 107086324 A | 8/2017 | |
| CN | 107851847 A | 3/2018 | |
| EP | 2851990 A1 * | 3/2015 | ............ H01M 10/05 |
| JP | 2000123867 A | 4/2000 | |
| JP | 2017117684 A | 6/2017 | |
| WO | 2017047554 A1 | 3/2017 | |

OTHER PUBLICATIONS

International Search Report of PCT Patent Application No. PCT/CN2020/070004 issued on Apr. 9, 2020.

* cited by examiner

*Primary Examiner* — Muhammad S Siddiquee

(57) ABSTRACT

To solve the problem that the existing non-aqueous electrolyte for a lithium ion battery cannot ensure the high-temperature storage performance and cycle performance at the same time, the invention provides a non-aqueous electrolyte for a lithium ion battery, comprising a solvent, a lithium salt and a compound represented by structural formula 1 and/or structural formula 2:

Structural formula 1

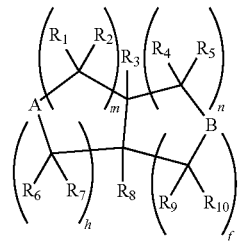

Structural formula 2

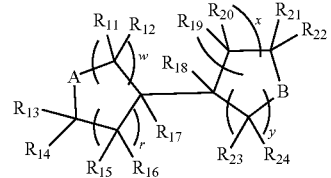

Meanwhile, the invention also discloses a lithium ion battery comprising the non-aqueous electrolyte for a lithium ion battery. The non-aqueous electrolyte provided by the invention can effectively improve the cycle performance and high-temperature storage performance of lithium ion batteries.

20 Claims, No Drawings

NON-AQUEOUS ELECTROLYTE FOR A LITHIUM ION BATTERY AND LITHIUM ION BATTERY

TECHNICAL FIELD

The invention belongs to the technical field of lithium ion batteries, and particularly relates to a non-aqueous electrolyte for a lithium ion battery and a lithium ion battery.

BACKGROUND

Compared with lead-acid batteries, nickel-hydrogen batteries or nickel-cadmium batteries, lithium-ion batteries have made great progress in the field of portable electronic products because of their advantages of high working voltage, high safety, long life and no memory effect. With the development of new energy vehicles, lithium ion batteries have great application prospects in the power supply system of new energy vehicles.

In the first charging process of a lithium ion battery, lithium salt and organic solvent would decompose on the electrode surface to form a passivation film, which may effectively inhibit the further decomposition of the organic solvent and lithium salt, and the passivation film is ion-conductive but electron-nonconductive. The characteristics (such as impedance and stability, etc.) of passivation film on the electrode surface have an important impact on the performances of lithium-ion battery. In the subsequent high-temperature storage or high-temperature cycle process, the SEI film would be constantly destroyed and repaired, while the electrolyte is constantly consumed and the internal resistance of the battery would gradually increase, eventually leading to a serious decline in battery performances. Many researchers have tried to improve the quality of SEI film by adding various negative film-forming additives (such as vinylene carbonate, fluoroethylene carbonate and ethylene carbonate) to electrolytes, to improve the performances of batteries. For example, Japanese Laid-Open Patent Application No. 2000-123867 proposes to improve battery performances by adding vinylene carbonate to electrolyte. Vinylene carbonate may undergo reduction and decomposition reaction before solvent molecules to form a passivation film on the surface of the negative electrode, to prevent the electrolyte from further decomposing on the electrode surface, thus improving the cycle performance of the battery. However, after the addition of vinylene carbonate, the battery is likely to generate gas during high-temperature storage, which leads to the battery expansion. In addition, the passivation film formed by vinylene carbonate has high impedance, especially at low temperature, which is likely to lead to precipitation of lithium during low temperature charging, affecting the safety of battery. Fluoroethylene carbonate may also form a passivation film on the surface of negative electrode, which would improve the cycle performance of battery. And the formed passivation film has low impedance, which could improve the low-temperature discharge performance of battery. However, fluoroethylene carbonate would generate more gas when stored at high temperature, which would obviously reduce the storage performance of battery at high temperature.

SUMMARY

The invention provides a non-aqueous electrolyte for a lithium ion battery and a lithium ion battery, aiming to solve the problem that the existing non-aqueous electrolyte for a lithium ion battery cannot ensure the high-temperature storage performance and cycle performance at the same time.

The technical solution adopted by the invention is as follows:

In one aspect, the invention provides a non-aqueous electrolyte for a lithium ion battery, including a solvent, a lithium salt and a compound represented by a structural formula 1 and/or a structural formula 2:

Structural formula 1

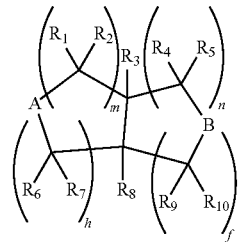

wherein A and B are each independently structural formula

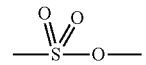

or structural formula

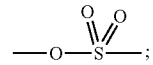

$R_1$, $R_2$, $R_3$, $R_4$, $R_5$, $R_6$, $R_7$, $R_8$, $R_9$ and $R_{10}$ are each independently selected from hydrogen, halogen, or a halogenated or non-halogenated organic group with 1-3 carbon atoms, m, n, h and f are 0, 1 or 2, and m+h≥1, n+f≥1;

Structural formula 2

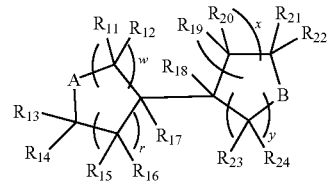

wherein A and B are each independently structural formula

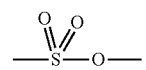

or structural formula

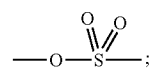

$R_{11}$, $R_{12}$, $R_{13}$, $R_{14}$, $R_{15}$, $R_{16}$, $R_{17}$, $R_{18}$, $R_{19}$, $R_{20}$, $R_{21}$, $R_{22}$, $R_{23}$ and $R_{24}$ are each independently selected from hydrogen, halogen or a halogenated or non-halogenated organic group with 1-3 carbon atoms, w, r, x and y are 0, 1 or 2, and w+r≥1, x+y≥1.

According to the non-aqueous electrolyte for a lithium ion battery provided by the invention, the compound represented by structural formula 1 and/or structural formula 2 is added. And the compound represented by structural formula 1 and/or structural formula 2 can take precedence over organic solvent, to obtain electrons on the surface of negative electrode and undergo reduction reaction to generate a passivation film during the charging process. It has a good film forming effect, thereby further inhibiting the decomposition of the organic solvent. In addition, the passivation film formed by the compound represented by structural formula 1 and/or structural formula 2 has better thermal stability, which could effectively inhibit the gas generation in the high-temperature storage process of battery, thereby improving the high-temperature storage performance and cycle performance of battery.

Optionally, the compound represented by structural formula 1 is selected from the following compounds:

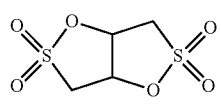

Compound 1

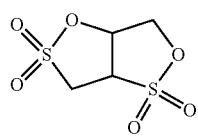

Compound 2

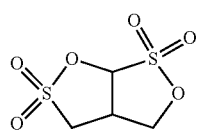

Compound 3

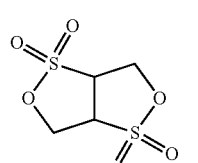

Compound 4

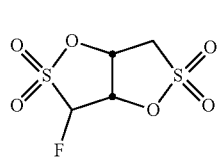

Compound 5

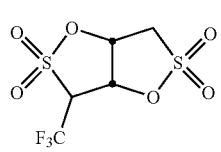

Compound 6

Optionally, the compound represented by structural formula 2 is selected from the following compounds:

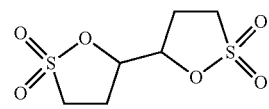

Compound 7

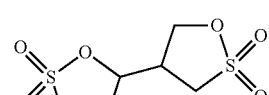

Compound 8

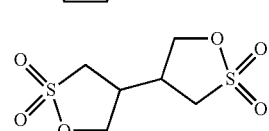

Compound 9

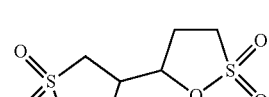

Compound 10

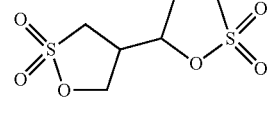

Compound 11

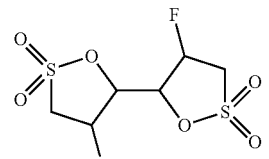

Compound 12

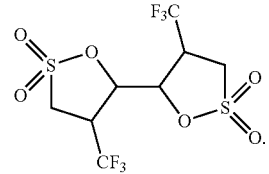

Optionally, based on the total mass of the non-aqueous electrolyte being 100%, the percentage mass of the compound represented by structural formula 1 and/or structural formula 2 is 0.1%-5.0%.

Optionally, the non-aqueous electrolyte of the lithium ion battery further includes one or more of unsaturated cyclic carbonate and fluorinated cyclic carbonate, cyclic sultone and cyclic sulfate.

Optionally, the unsaturated cyclic carbonate includes one or more of vinylene carbonate, vinylethylene carbonate and methylene vinyl carbonate;

the fluorinated cyclic carbonate includes one or more of fluoroethylene carbonate, trifluoromethyl vinylethylene carbonate and bisfluoroethylene carbonate;

the cyclic sultone includes one or more of 1,3-propane sultone, 1,4-butane sultone and propenyl-1,3-sultone;

the cyclic sulfate includes one or more of ethylene sulfate and 4-methyl ethylene sulfate.

In the non-aqueous electrolyte for a lithium ion battery, the content of the unsaturated cyclic carbonate is 0.01-10%; the content of the fluorinated cyclic carbonate is 0.01-10%; the content of the cyclic sultone is 0.01-10%; the content of the cyclic sulfate is 0.01-10%.

Optionally, the solvent is a mixture of cyclic carbonate and chain carbonate.

Optionally, the lithium salt is selected from one or more of $LiPF_6$, $LiBF_4$, LiBOB, LiDFOB, $LiN(SO_2CF_3)_2$ or $LiN(SO_2F)_2$.

In another aspect, the invention also provides a lithium ion battery, including a positive electrode, a negative electrode, and the non-aqueous electrolyte for a lithium ion battery.

Optionally, the positive electrode comprises a positive electrode active material, and the positive electrode active material is at least one of $LiNi_xCo_yMn_zL_{(1-x-y-z)}O_2$, $LiCo_xL_{(1-x')}O_2$, $LiNi_{x'}L'_{y'}Mn_{(2-x''-y')}O_4$ and $Li_zMPO_4$, L is at least one of Al, Sr, Mg, Ti, Ca, Zr, Zn, Si or Fe, $0 \leq x \leq 1$, $0 \leq y \leq 1$, $0 \leq z \leq 1$, $0 < x+y+z \leq 1$, $0 < x' \leq 1$, $0.3 \leq x'' \leq 0.6$, $0.01 \leq y' \leq 0.2$, L' is at least one of Co, Al, Sr, Mg, Ti, Ca, Zr, Zn, Si and Fe; $0.5 \leq z' \leq 1$, M is at least one of Fe, Mn and Co.

DETAILED DESCRIPTION OF DISCLOSED EMBODIMENTS

In order to make the technical problems to be solved, technical solutions and beneficial effects more apparent and clearer, the present application will be described in further detail below with reference to embodiments. It should be understood that the specific embodiments described herein are only for the purpose of explaining the present invention and are not intended to limit the present invention.

An embodiment of the invention provides a non-aqueous electrolyte for a lithium ion battery, including a solvent, a lithium salt and a compound represented by structural formula 1 and/or a structural formula 2:

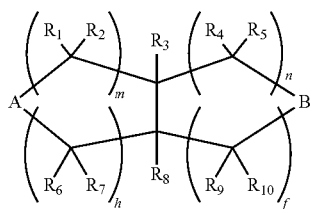

Structural formula 1 wherein A and B are each independently structural formula

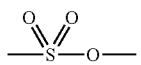

or structural formula

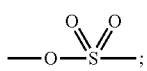

$R_1$, $R_2$, $R_3$, $R_4$, $R_5$, $R_6$, $R_7$, $R_8$, $R_9$ and $R_{10}$ are each independently selected from hydrogen, halogen, or a halogenated or non-halogenated organic group with 1-3 carbon atoms, m, n, h and f are 0, 1 or 2, and $m+h \geq 1$, $n+f \geq 1$;

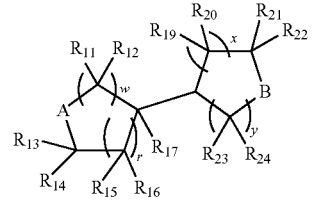

Structural formula 2 wherein A and B are each independently structural formula

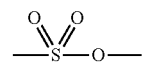

or structural formula

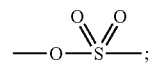

$R_{11}$, $R_{12}$, $R_{13}$, $R_{14}$, $R_{15}$, $R_{16}$, $R_{17}$, $R_{18}$, $R_{19}$, $R_{20}$, $R_{21}$, $R_{22}$, $R_{23}$ and $R_{24}$ are each independently selected from hydrogen, halogen or a halogenated or non-halogenated organic group with 1-3 carbon atoms, w, r, x and y are 0, 1 or 2, and $w+r \geq 1$, $x+y \geq 1$.

In some embodiments, the compound represented by structural formula 1 is selected from the following compounds:

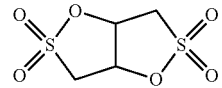

Compound 1

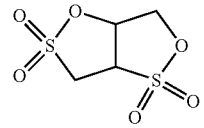

Compound 2

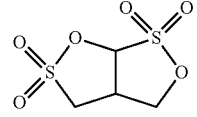

Compound 3

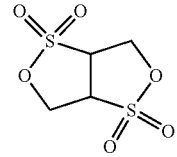

Compound 4

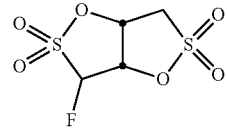

Compound 5

-continued

Compound 6

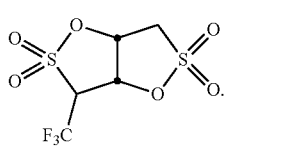

In some embodiments, the compound represented by structural formula 2 is selected from the following compounds:

Compound 7

Compound 8

Compound 9

Compound 10

Compound 11

Compound 12

It should be noted that the above are some of the compounds claimed by the present invention. The compounds are not limited to the above, and it should not be understood as limiting the present invention.

In some embodiments, based on the total mass of the non-aqueous electrolyte being 100%, the percentage mass content of the compound represented by structural formula 1 and/or structural formula 2 is 0.1%-5.0%. Specifically, based on the total mass of the non-aqueous electrolyte being 100%, the percentage mass content of the compounds represented by structural formula 1 and/or structural formula 2 may be 0.1%, 0.3%, 0.6%, 1%, 1.2%, 1.5%, 1.8%, 2.0%, 2.3%, 2.6%, 2.9%, 3.1%, 3.5%, 3.7%, 4.0%, 4.3%, 4.5%, 4.8% or 5.0%.

In some embodiments, the non-aqueous electrolyte for a lithium ion battery further includes one or more of unsaturated cyclic carbonate and fluorinated cyclic carbonate, cyclic sultone and cyclic sulfate.

In a more preferred embodiment, the unsaturated cyclic carbonate includes one or more of vinylene carbonate (VC, CAS: 872-36-6), vinylethylene carbonate (CAS: 4427-96-7) and methylene vinyl carbonate (CAS: 124222-05-5).

The fluorinated cyclic carbonate includes one or more of fluoroethylene carbonate (FEC, CAS: 114435-02-8), trifluoromethyl vinylethylene carbonate (CAS: 167951-80-6) and bisfluoroethylene carbonate (CAS: 311810-76-1).

The cyclic sultone is selected from one or more of 1,3-propane sultone (CAS: 1120-71-4), 1,4-butane sultone (CAS: 1633-83-6) and propenyl-1,3-sultone (CAS: 21806-61-1).

The cyclic sulfate is selected from one or more of ethylene sulfate (CAS: 1072-53-3) and 4-methyl ethylene sulfate (CAS: 5689-83-8).

In some embodiments, the solvent is a mixture of cyclic carbonate and chain carbonate.

In a more preferred embodiment, the cyclic carbonate is selected from one or more of ethylene carbonate, propylene carbonate and butylene carbonate.

The chain carbonate is selected from one or more of dimethyl carbonate, diethyl carbonate, methyl ethyl carbonate and methyl propyl carbonate.

The lithium salt is selected from one or more of $LiPF_6$, $LiBF_4$, LiBOB, LiDFOB, $LiN(SO_2CF_3)_2$ and $LiN(SO_2F)_2$. The content of the lithium salt can be varied within a wide range, and preferably, the content of the lithium salt in the non-aqueous electrolyte for a lithium ion battery is 0.1-15%.

Another embodiment of the present invention provides a lithium ion battery, including a positive electrode, a negative electrode and the non-aqueous electrolyte for a lithium ion battery as described above.

The positive electrode active material is at least one of $LiNi_xCo_yMn_zL_{(1-x-y-z)}O_2$, $LiCo_xL_{(1-x)}O_2$, $LiNi_{x'}L'_{y'}Mn_{(2-x''-y')}O_4$ and $Li_zMPO_4$, L is at least one of Al, Sr, Mg, Ti, Ca, Zr, Zn, Si or Fe, $0 \leq x \leq 1$, $0 \leq y \leq 1$, $0 \leq z \leq 1$, $0 < x+y+z \leq 1$, $0 < x' \leq 1$, $0.3 \leq x'' \leq 0.6$, $0.01 \leq y' \leq 0.2$, L' is at least one of Co, Al, Sr, Mg, Ti, Ca, Zr, Zn, Si and Fe; $0.5 \leq z' \leq 1$, M is at least one of Fe, Mn and Co.

The positive electrode further includes a positive current collector for extracting current, and the positive electrode active material covers the positive current collector.

The negative electrode includes a negative electrode active material which can be made of carbon materials, metal alloys, lithium-containing oxides and silicon-containing materials.

The negative electrode further includes a negative current collector for extracting current, and the negative electrode active material covers the negative current collector.

In some embodiments, a separator is further arranged between the positive electrode and the negative electrode, which is a conventional separator in the field of lithium ion batteries, so it will not be described in the present application.

With the above-described non-aqueous electrolyte, the lithium ion battery provided by the embodiments of the invention could effectively solve the cycle performance problem of lithium ion battery and improve the electrochemical performance of lithium ion battery.

The present invention will be further elaborated by the following embodiments.

Embodiment 1

The embodiment is used for explaining the non-aqueous electrolyte for a lithium ion battery, the lithium ion battery and the preparation methods thereof disclosed by the invention, which includes the following steps:

1) Preparation of the Non-Aqueous Electrolyte

Ethylene carbonate (EC), diethyl carbonate (DEC) and ethyl methyl carbonate (EMC) were mixed according to the mass ratio of EC:DEC:EMC=1:1:1, then lithium hexafluorophosphate ($LiPF_6$) was added until the molar concentration was 1 mol/L, and then based on the total mass of the non-aqueous electrolyte being 100%, the components with the percentage mass content shown in Embodiment 1 in Table 1 was added.

2) Preparation of Positive Electrode Plate

According to the mass ratio of 93:4:3, the positive electrode active material lithium nickel cobalt manganese oxide ($LiNi_{0.5}Co_{0.2}Mn_{0.3}O_2$), conductive carbon black Super-P and binder polyvinylidene fluoride (PVDF) were mixed, and then the mixture was dispersed in N-methyl-2-pyrrolidone (NMP) to obtain a positive electrode slurry. The positive electrode slurry was uniformly coated on both sides of aluminum foil, then dried, calendered and vacuum dried, and then aluminum lead wire was welded by ultrasonic welding machine to obtain a positive electrode plate, the thickness of the positive electrode plate is 120-150 μm.

3) Preparation of Negative Electrode Plate

According to the mass ratio of 94:1:2.5:2.5, the negative electrode active material artificial graphite, conductive carbon black Super-P, binder styrene butadiene rubber (SBR) and carboxymethyl cellulose (CMC) were mixed, and then the mixture was dispersed in deionized water to obtain a negative electrode slurry. The slurry was coated on both sides of copper foil, then dried, calendered and vacuum dried, and then nickel lead wire was welded by ultrasonic welding machine to obtain a negative electrode plate, the thickness of the negative electrode plate is 120-150 μm.

4) Preparation of Battery Core

A three-layer separator film with a thickness of 20 μm was arranged between the positive electrode plate and the negative electrode plate, and then the laminated structure consisting of the positive electrode plate, the negative electrode plate and the separator was wound to obtain a wound body. Then the wound body was flattened and put into an aluminum foil packaging bag, baked in vacuum at 85° C. for 24 h to obtain a core to be injected with liquid.

5) Liquid Injection and Formation of the Battery Core

In a glove box with the dew point controlled below −40° C., the non-aqueous electrolyte prepared above was injected into the battery core, then sealed in vacuum and allowed to stand for 24 h.

Then, the routine formation of First Charge was performed according to the following steps: charged with 0.05 C constant current for 180 min, then charged to 3.95V with 0.2 C constant current, secondary vacuum sealing, then further charged to 4.2V with 0.2 C constant current, after being left at normal temperature for 24 hours, discharged to 3.0V with 0.2 C constant current, then a 4.2V $LiNi_{0.5}Co_{0.2}Mn_{0.3}O_2$/artificial graphite lithium ion battery was obtained.

Embodiments 2-10

Embodiments 2-10 are used to illustrate the non-aqueous electrolyte for a lithium ion battery, the lithium ion battery and the preparation methods thereof disclosed in the present application, which include most of the steps of Embodiment 1, with the following differences:

In the preparation steps of the non-aqueous electrolyte:
based on the total mass of the non-aqueous electrolyte being 100%, the non-aqueous electrolytes were added with the components with the percentage mass contents shown in Embodiments 2-10 in Table 1.

Comparative Examples 1-6

Comparative Examples 1-6 are used for comparing and explaining the non-aqueous electrolyte for a lithium ion battery, the lithium ion battery and the preparation methods thereof disclosed by the present application, which include most of the steps of Embodiment 1, with the following differences:

In the preparation steps of the non-aqueous electrolyte:
based on the total mass of the non-aqueous electrolyte being 100%, the non-aqueous electrolytes were added with the components with the percentage mass contents shown in Comparative Examples 1-6 in Table 1.

Performance Tests

The lithium ion batteries prepared in Embodiments 1-10 and Comparative Examples 1-16 were tested for the following performances:

1) High-Temperature Cycle Performance Test

At 45° C., the formed battery was charged to 4.2V with 1 C constant current/constant voltage, the cut-off current was 0.01 C, and then discharged to 3.0V with 1 C constant current. The above step was repeated, after N cycles of charge/discharge, the capacity retention rate of the Nth cycle was calculated to evaluate its high-temperature cycle performance.

The formula for calculating the Nth cycle capacity retention rate at 45° C. 1 C is as follows:

The $N$th cycle capacity retention rate (%)=(discharge capacity of the $N$th cycle/discharge capacity of the first cycle)×100%.

2) High-Temperature (60° C.) Storage Performance Test

The formed battery was charged to 4.2V at normal temperature with 1 C constant current, the cut-off current was 0.01 C, then discharged to 3.0V with 1 C constant current, and its initial discharge capacity was measured. Then the battery was charged to 4.2V with 1 C constant current/constant voltage, the cut-off current was 0.01 C, and the initial thickness was measured. Then, after the battery was stored at 60° C. for N days, the thickness of the battery was measured again, and then the battery was discharged to 3.0V with 1 C constant current, and its retention capacity was measured. Then, the battery was charged to 4.2V with 1 C constant current/constant voltage, the cut-off current was 0.01 C, and then discharged to 3.0V with 1 C constant current, and its recovery capacity was measured. The calculation formulas of capacity retention rate and capacity recovery rate are as follows:

Capacity retention rate (%)=retention capacity/initial capacity×100%;

Capacity recovery rate (%)=recovery capacity/initial capacity×100%;

Thickness expansion rate (%)=(battery thickness after storage for $N$ days−initial battery thickness)/initial battery thickness×100%.

The test results are shown in Table 1.

TABLE 1

| Embodiments/ Comparative Examples | Compounds represented by structural formula 1/ structural formula 2 and contents | Other additives and contents | After 30 days of storage at 60° C. | | | 500th cycle capacity retention rate at 45° C. 1 C |
|---|---|---|---|---|---|---|
| | | | Capacity retention rate | Capacity recovery rate | Thickness expansion rate | |
| Embodiment 1 | Compound 1: 0.2% | — | 80.5% | 85.7% | 12.4% | 74.3% |
| Embodiment 2 | Compound 3: 0.5% | — | 82.8% | 89.4% | 10.4% | 80.2% |
| Embodiment 3 | Compound 5: 0.5% | — | 85.2% | 90.3% | 11.5% | 83.8% |
| Embodiment 4 | Compound 7: 0.5% | — | 79.4% | 84.8% | 13.1% | 76.9% |
| Embodiment 5 | Compound 9: 1% | — | 83.3% | 88.7% | 9.5% | 79.2% |
| Embodiment 6 | Compound 11: 0.5% | — | 85.6% | 91.7% | 7.5% | 80.2% |
| Embodiment 7 | Compound 1: 0.2% | Vinylene carbonate: 1% | 83.9% | 88.7% | 15.6% | 83.9% |
| Embodiment 8 | Compound 1: 0.2% | Fluoroethylene carbonate: 1% | 80.3% | 86.4% | 18.6% | 84.4% |
| Embodiment 9 | Compound 1: 0.2% | Ethylene sulfate: 1% | 85.9% | 90.7% | 11.5% | 83.1% |
| Embodiment 10 | Compound 1: 0.2% | LiN(SO$_2$F)$_2$: 1% | 82.7% | 87.6% | 13.8% | 82.5% |
| Comparative Example 1 | — | — | 65.1% | 70.5% | 25.6% | 60.7% |
| Comparative Example 2 | — | Vinylene carbonate: 1% | 68.1% | 7.5% | 30.5% | 75.6% |
| Comparative Example 3 | — | Fluoroethylene carbonate: 1% | 64.2% | 71.7% | 35.4% | 75.4% |
| Comparative Example 5 | — | Ethylene sulfate: 1% | 78.7% | 83.5% | 18.4% | 73.8% |
| Comparative Example 6 | — | LiN(SO$_2$F)$_2$: 1% | 73.9% | 79.4% | 20.4% | 71.9% |

Comparing the test results of Embodiments 1-6 and Comparative Example 1 in Table 1, it can be seen that adding the compound represented by structural formula 1 or structural formula 2 provided by the present application into the non-aqueous electrolyte can effectively improve the high-temperature cycle performance and high-temperature storage performance of the lithium ion battery.

Comparing the test results of Embodiments 7-10 and Comparative Examples 2-6 in Table 1, it can be seen that adding the compound represented by structural formula 1 or structural formula 2 into the electrolyte containing the existing additives can further improve the high-temperature cycle performance and high-temperature storage performance of the battery.

In this specification and the appended claims, the singular forms "a," "an," and "the" include plural reference, unless the context clearly dictates otherwise. The above descriptions are only preferred embodiments and are not intended to limit the present invention. Any modifications, equivalent substitutions and improvements made within the spirit and principles of the present invention shall be included within the scope of protection of the present invention.

The invention claimed is:

1. A non-aqueous electrolyte for a lithium ion battery, comprising a solvent, a lithium salt and a compound represented by structural formula 1 and/or structural formula 2:

Structural formula 1

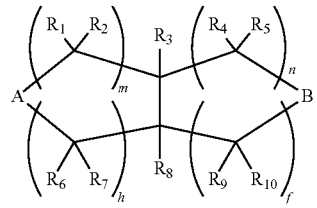

wherein A and B are each independently structural formula

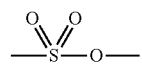

or structural formula

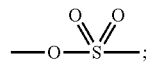

$R_1$, $R_2$, $R_3$, $R_4$, $R_5$, $R_6$, $R_7$, $R_8$, $R_9$ and $R_{10}$ are each independently selected from hydrogen, halogen, or a halogenated or non-halogenated organic group with 1-3 carbon atoms, m, n, h and f are 0, 1 or 2, and m+h≥1, n+f≥1;

Structural formula 2

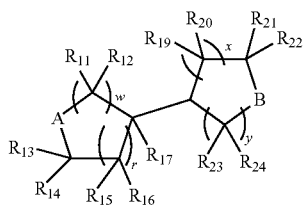

wherein A and B are each independently structural formula

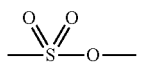

or structural formula

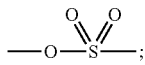

;

$R_{11}$, $R_{12}$, $R_{13}$, $R_{14}$, $R_{15}$, $R_{16}$, $R_{17}$, $R_{18}$, $R_{19}$, $R_{20}$, $R_{21}$, $R_{22}$, $R_{23}$ and $R_{24}$ are each independently selected from hydrogen, halogen or a halogenated or non-halogenated organic group with 1-3 carbon atoms, w, r, x and y are 0, 1 or 2, and $w+r \geq 1$, $x+y \geq 1$.

2. The non-aqueous electrolyte for a lithium ion battery of claim 1, wherein the compound represented by structural formula 1 is selected from the following compounds:

Compound 1

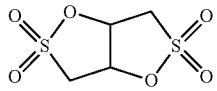

Compound 2

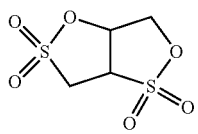

Compound 3

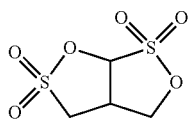

Compound 4

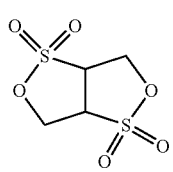

Compound 5

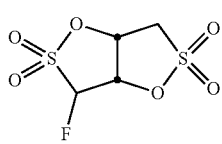

Compound 6

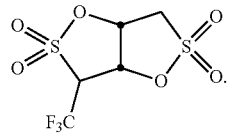

.

3. The non-aqueous electrolyte for a lithium ion battery of claim 1, wherein the compound represented by structural formula 2 is selected from the following compounds:

Compound 7

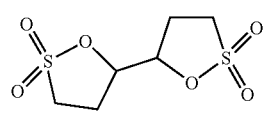

Compound 8

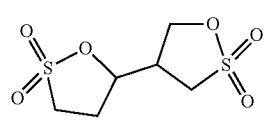

Compound 9

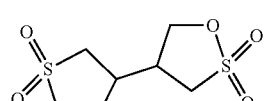

Compound 10

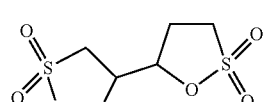

Compound 11

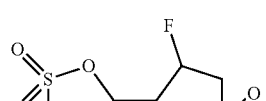

Compound 12

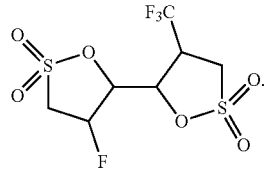

.

4. The non-aqueous electrolyte for a lithium ion battery of claim 1, wherein the percentage mass content of the compound represented by structural formula 1 and/or structural formula 2 is 0.1%-5.0% based on the total mass of the non-aqueous electrolyte being 100%.

5. The non-aqueous electrolyte for a lithium ion battery of claim 1, further comprising one or more of unsaturated cyclic carbonate and fluorinated cyclic carbonate, cyclic sultone and cyclic sulfate.

6. The non-aqueous electrolyte for a lithium ion battery of claim 5, wherein the unsaturated cyclic carbonate comprises one or more of vinylene carbonate, vinylethylene carbonate and methylene vinyl carbonate;
the fluorinated cyclic carbonate comprises one or more of fluoroethylene carbonate, trifluoromethyl vinylethylene carbonate and bisfluoroethylene carbonate;
the cyclic sultone comprises one or more of 1,3-propane sultone, 1,4-butane sultone and propenyl-1,3-sultone;

the cyclic sulfate comprises one or more of ethylene sulfate and 4-methyl ethylene sulfate.

7. The non-aqueous electrolyte for a lithium ion battery of claim 5, wherein in the non-aqueous electrolyte for a lithium ion battery, the content of the unsaturated cyclic carbonate is 0.01-10%; the content of the fluorinated cyclic carbonate is 0.01-10%; the content of the cyclic sultone is 0.01-10%; the content of the cyclic sulfate is 0.01-10%.

8. The non-aqueous electrolyte for a lithium ion battery of claim 1, wherein the lithium salt is selected from one or more of $LiPF_6$, $LiBF_4$, LiBOB, LIDFOB, $LiN(SO_2CF_3)_2$ or $LiN(SO_2F)_2$.

9. A lithium ion battery, comprising a positive electrode, a negative electrode, and the non-aqueous electrolyte for a lithium ion battery of claim 1.

10. The lithium ion battery of claim 9, wherein the positive electrode comprises a positive electrode active material, and the positive electrode active material is at least one of $LiNi_xCO_yMn_zL_{(1-x-y-z)}O_2$, $LiCo_xL_{(1-x')}O_2$, $LiNi_{x''}L'_yMn_{(2-x''-y')}O_4$ and $Li_zMPO_4$, L is at least one of Al, Sr, Mg, Ti, Ca, Zr, Zn, Si or Fe, 0≤x≤1, 0≤y≤1, 0≤z≤1, 0<x+y+z≤1, 0<x'≤1, 0.3≤x"≤0.6, 0.01≤y'≤0.2, L' is at least one of Co, Al, Sr, Mg, Ti, Ca, Zr, Zn, Si and Fe; 0.5≤z'≤1, M is at least one of Fe, Mn and Co.

11. The non-aqueous electrolyte for a lithium ion battery of claim 2, wherein the percentage mass content of the compound represented by structural formula 1 and/or structural formula 2 is 0.1%-5.0% based on the total mass of the non-aqueous electrolyte being 100%.

12. The non-aqueous electrolyte for a lithium ion battery of claim 3, wherein the percentage mass content of the compound represented by structural formula 1 and/or structural formula 2 is 0.1%-5.0% based on the total mass of the non-aqueous electrolyte being 100%.

13. The non-aqueous electrolyte for a lithium ion battery of claim 6, wherein in the non-aqueous electrolyte for a lithium ion battery, the content of the unsaturated cyclic carbonate is 0.01-10%; the content of the fluorinated cyclic carbonate is 0.01-10%; the content of the cyclic sultone is 0.01-10%; the content of the cyclic sulfate is 0.01-10%.

14. A lithium ion battery, comprising a positive electrode, a negative electrode, and the non-aqueous electrolyte for a lithium ion battery of claim 2.

15. A lithium ion battery, comprising a positive electrode, a negative electrode, and the non-aqueous electrolyte for a lithium ion battery of claim 3.

16. A lithium ion battery, comprising a positive electrode, a negative electrode, and the non-aqueous electrolyte for a lithium ion battery of claim 4.

17. A lithium ion battery, comprising a positive electrode, a negative electrode, and the non-aqueous electrolyte for a lithium ion battery of claim 5.

18. A lithium ion battery, comprising a positive electrode, a negative electrode, and the non-aqueous electrolyte for a lithium ion battery of claim 6.

19. A lithium ion battery, comprising a positive electrode, a negative electrode, and the non-aqueous electrolyte for a lithium ion battery of claim 7.

20. A lithium ion battery, comprising a positive electrode, a negative electrode, and the non-aqueous electrolyte for a lithium ion battery of claim 8.

* * * * *